(12) United States Patent
Brown

(10) Patent No.: US 9,173,731 B2
(45) Date of Patent: Nov. 3, 2015

(54) SEGMENTED HERNIA PATCH FRAME

(76) Inventor: Roderick B. Brown, Glenwood, MN (US)

(*) Notice: Subject to any disclaimer, the term of this patent is extended or adjusted under 35 U.S.C. 154(b) by 455 days.

(21) Appl. No.: 13/595,182

(22) Filed: Aug. 27, 2012

(65) Prior Publication Data

US 2014/0058416 A1 Feb. 27, 2014

(51) Int. Cl.
*A61F 2/00* (2006.01)

(52) U.S. Cl.
CPC .................................. *A61F 2/0063* (2013.01)

(58) Field of Classification Search
CPC . A61F 2/0063; A61F 2/88; A61F 2002/0068; A61F 2002/0072; A61F 2002/821
USPC ...................... 623/1.11; 57/80; 604/372, 373; 606/151, 148, 153, 139, 142, 228, 223, 606/232, 229–231; 600/37
See application file for complete search history.

(56) References Cited

U.S. PATENT DOCUMENTS

| | | | |
|---|---|---|---|
| 5,824,082 A * | 10/1998 | Brown | 623/11.11 |
| 2006/0064175 A1 * | 3/2006 | Pelissier et al. | 623/23.72 |
| 2007/0265710 A1 | 11/2007 | Brown | |
| 2010/0261956 A1 * | 10/2010 | Townsend et al. | 600/37 |

* cited by examiner

*Primary Examiner* — Jocelin Tanner
(74) *Attorney, Agent, or Firm* — Nikolai & Mersereau, P.A.; Thomas J. Nikolai

(57) ABSTRACT

A hernia repair prosthesis comprises a segmented frame forming a closed loop where a first segment comprises a helical hollow tube and a second segment comprises a solid strand. Both segments are preferably a metal exhibiting shape memory properties and the two segments are assembled with end portions of the second segment inserted into the lumen at opposed end portions of the first segment with a clearance fit. A prosthetic fabric is attached to the segmented frame.

10 Claims, 3 Drawing Sheets

SEGMENTED HERNIA PATCH FRAME

BACKGROUND OF THE INVENTION

I. Field of the Invention

This invention relates generally to a prosthesis for the repair of hernias, and more particularly to an improved hernia repair patch, deliverable in a rolled form through a trocar in an endoscopic procedure and which deploys, when unconstrained, to a somewhat planar configuration.

II. Discussion of the Prior Art

In U.S. Pat. No. 5,824,082, I disclose a hernia repair patch comprising a single strand, closed loop, wire frame made of a shape memory alloy on which is attached a prosthetic mesh. That device was intended for deployment through a trocar in the course of an endoscopic hernia repair procedure. It was found that this prosthesis was somewhat difficult to deliver through a trocar of a sufficiently small diameter felt appropriate for use in typical endoscopic hernia repair surgery.

I later learned that a multifilar cable of Nitinol® strands as the frame allowed a more compact device when rolled for insertion, via a cannula, and this improvement is described in currently pending application Ser. No. 11/431,171, filed May 10, 2006 (published application US 2007/0265710 A1). That device has been commercialized as the REBOUND hernia repair patch available from Minnesota Medical Development, Inc. of Minnetonka, Minn.

In very few cases, upon patient follow-up, x-rays revealed instances where strands comprising the cable frame had broken, but without any harm whatsoever to the patients. It has been theorized that the breakage may have been as result of fatigue due to stresses on the frame induced by body motion and flexures following the complete integration of the hernia patch into the surrounding tissue by normal tissue in-growth. Even though the observed instances of frame breakage have been small and have not resulted in any adverse patient outcomes, to alleviate any potential concern by surgeons, patients or regulatory authorities, I have now conceived of a solution that should avoid stress-induced fractures in hernia patch frames.

SUMMARY OF THE INVENTION

In accordance with the present invention, a hernia repair prosthesis comprises a segmented frame forming a closed loop where a first segment of the frame comprises a helical, hollow, tubular metal strand and a second segment comprises a solid metal strand. In forming the frame, opposed end portions of the second segment are inserted into opposed end portions of the first segment and are slidable therein. A prosthetic fabric is attached to the segmented frame. Following surgical implant, any stresses that might otherwise has been created in the frame are resolved in that the frame segments are permitted to move telescopically with respect to one another so that flexure of the frame at what would otherwise be a stress point is avoided.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
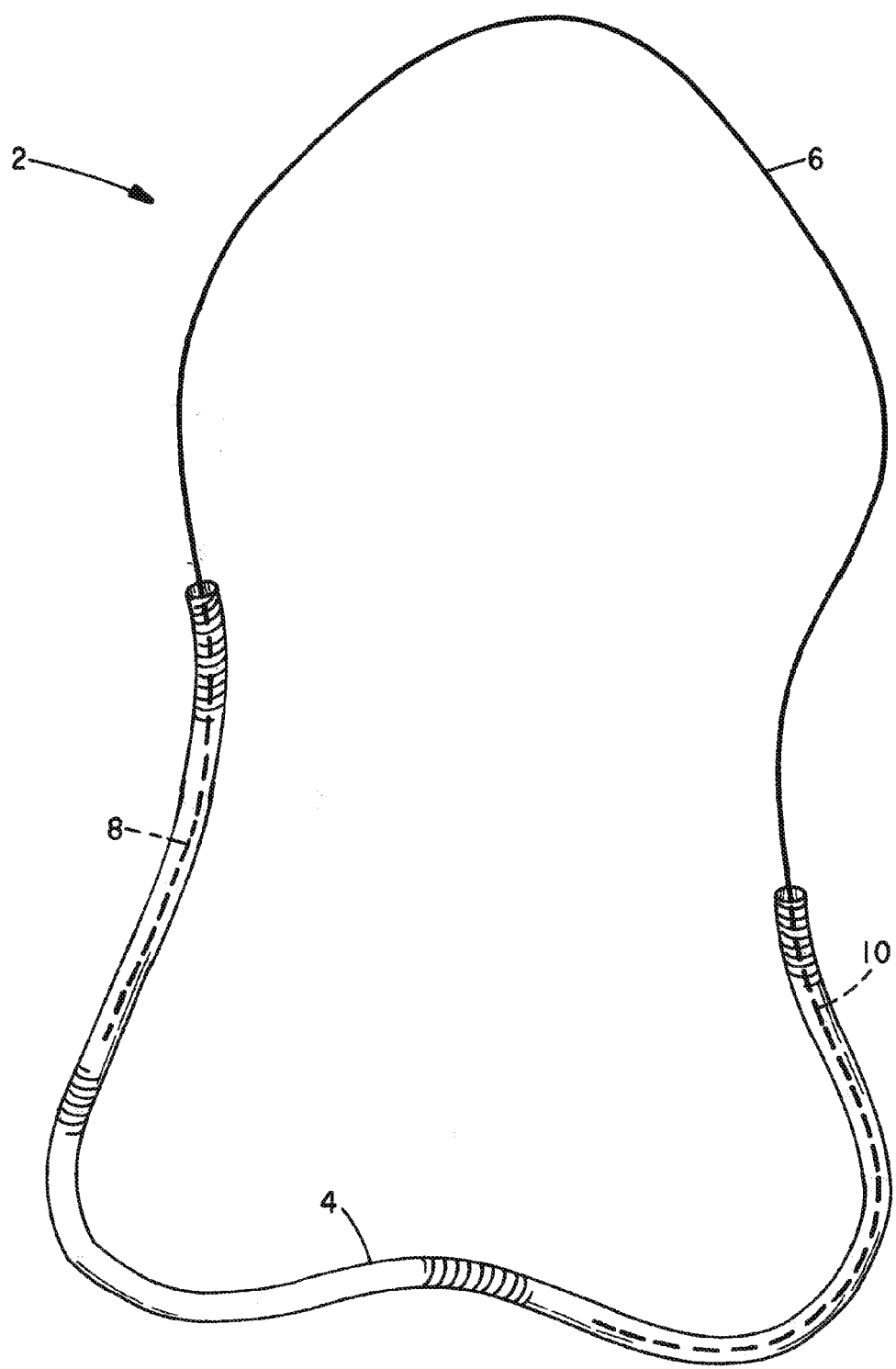
FIG. 1 is a perspective view of a hernia repair prosthesis constructed in accordance with the present invention.

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise.

In FIG. 1 the frame portion of a hernia repair prosthesis is indicated generally by numeral 2 and is seen to comprise a segmented frame forming a closed loop where a first segment 4 comprises a helical hollow tubular metal strand and a second segment 6 comprises a solid metal strand. The segment 4 is preferably of a type manufactured and sold by Fort Wayne Metals Inc. of Fort Wayne, Ind., and sold under the trademark, HHS®, an acronym for helical hollow strand.

Figure 2:
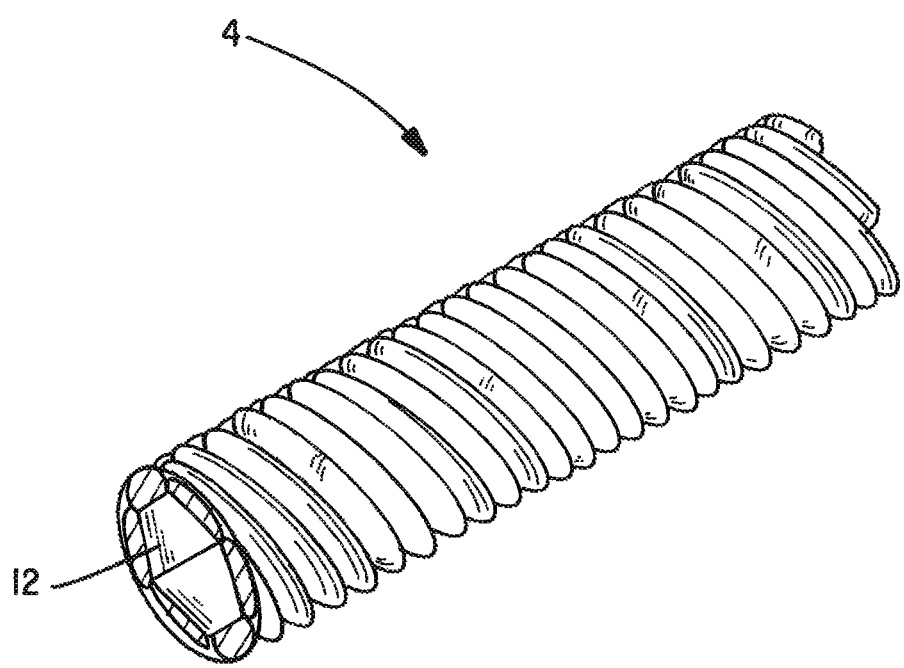
FIG. 2 is a perspective drawing showing a portion of the frame comprising a helical, hollow, tubular metal strand.

FIG. 2 is a perspective view of the HHS tubing that comprises six filars arranged in a single layer and, for the present application, the filars are preferably a nickel titanium alloy exhibiting shape memory properties. A suitable hernia patch may employ a Nitinol® strand 4 like that illustrated in FIG. 2 where the outer diameter may be in a range from 0.0025 inch to 0.25 inch while the strand 6 which may be a solid Nitinol wire or a cable formed from multi-strands and having an outside diameter in a range from 0.0024 inch to 0.24 inch. In forming the frame 2, the segments 4 and 6 may be heat-set in a suitable mold so as to exhibit a desired shape configuration in the manner more fully explained in the aforementioned published application US 2007/02365710 A1. The alloy is preferably such that the Nitinol used exhibits a transformation temperature at close to boy temperature (37° C.).

With continued reference to FIG. 1, opposed end portions 8 and 10 of the second segment 6 are shown inserted into the lumen 12 (FIG. 2) of the first segment 4. The tolerances are such between the outer diameter of the solid strand 6 and the inner diameter of the helical hollow strand 4 such that there is sufficient clearance permitting the two segments to slide relative to one another.

Figure 3:
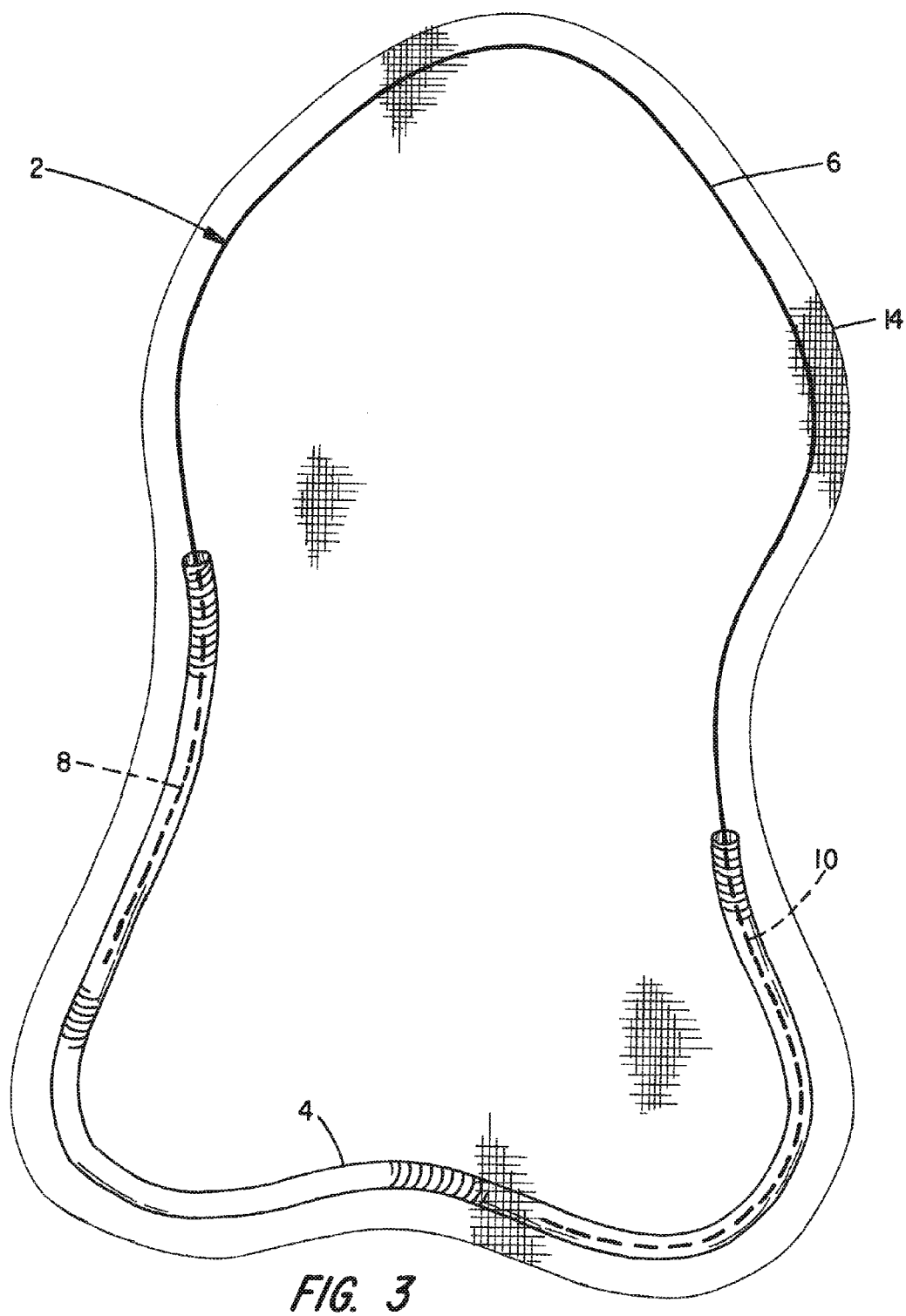
FIG. 3 is a view like that of FIG. 1 but with a prosthetic fabric attached to the frame.

FIG. 3 shows the frame 2 in assembled form as shown in FIG. 1 and with a prosthetic fabric 14 attached to the segmented frame 2. The prosthetic fabric is preferably a woven or a non-woven mesh of polypropylene, but also may be an expanded polytetrafluoroethylene material, a polyester or any other approved fabric or biological material suitable for hernia and soft tissue repair. The fabric may be affixed to the frame 2 by stitching, or alternatively by thermal bonding, adhesive bonding or ultrasonic bonding.

From what has been described, those skilled in the art can appreciate that when the hernia patch of FIG. 3 is delivered into the abdominal cavity in a rolled form and allowed to expand and used to repair either a ventral hernia or an inguinal hernia, within a matter of weeks from surgical placement in an endoscopic procedure, tissue in-growth through the mesh results in incorporation of the hernia patch into surrounding muscle and fascial tissue at the repair site. Because the coupled segments 4 and 6 comprising the frame 2 are able to slide relative to one another, any stress that might otherwise be imposed and resulting in ultimate fatigue failure of one or more strands of the segment 6 is relieved due to the yielding action allowed by the frame construction of the present invention.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, instead of using HHS tubing, the strand 4 may comprise thin, solid wall tubing of a shape memory alloy. Likewise, the strand 6 may be a single wire, a multi-strand cable or a hollow tube of a lesser diameter than the I.D. of the tubular strand 4 that is employed. Also, while FIGS. 1 and 3 illustrate a two member frame, it is also contemplated that the frame can be further segmented by using multiple strands like 4 and 6 coupled to one another in the manner shown with end portions of the strand 6 inserted into the lumens of adjacently positioned strands 4.

What is claimed is:

1. A hernia repair prosthesis comprising:
   (a) a segmented frame of at least two pieces where a first piece comprises a metal strand wound as a helix and forming an elongate tube with a lumen and a second piece comprises a metal strand with opposed end portions of the second piece inserted into opposed end portions of the first piece and slidable in the lumen to form a closed loop; and
   (b) a prosthetic fabric attached to the segmented frame.

2. The hernia repair prosthesis of claim 1 wherein the first and second pieces comprise a shape memory alloy.

3. The hernia repair prosthesis of claim 2 wherein the second piece comprises plural, strands twisted as a cable.

4. The hernia repair prosthesis of claim 2 wherein the shape memory alloy exhibits a transformation temperature of about 37'C.

5. The hernia repair prosthesis of claim 1 wherein the opposed ends of the second piece fit within the lumen of the first piece with a predetermined clearance fit.

6. The hernia repair prosthesis of claim 1 wherein the prosthetic fabric is selected from a group consisting of a woven or a non-woven mesh of polypropylene expanded polytetrafluoroethylene, polyester and a biological material.

7. The hernia repair prosthesis of claim 1 wherein the prosthetic fabric is affixed to the segmented frame by one of stitching, thermal bonding, adhesive bonding and ultrasonic bonding.

8. The hernia repair prosthesis of claim 1 wherein the elongate tube has an outer diameter in a range of from 0.0025 inch to 0.25 inch and an inner diameter in a range of from 0.0015 inch to 0.20 inch.

9. The hernia repair prosthesis of claim 8 wherein the metal strand comprising the second piece has an outer diameter in a range of from 0.0024 inch to 0.24 inch.

10. A hernia repair prosthesis comprising:
    (a) a segmented frame having at least one first segment and at least one second segment where the at least one first segment comprises a strand of metal wound as a helix and forming an elongate tube with a lumen and the at least one second segment comprises a metal strand having an end portion thereof inserted into the lumen of the at least one first segment and telescopingly movable therein, the at least one first segment and the at least one second segment together forming a closed loop; and
    (b) a prosthetic fabric attached to the segmented frame.

* * * * *